(12) United States Patent
Hogan

(10) Patent No.: US 7,751,862 B2
(45) Date of Patent: Jul. 6, 2010

(54) FREQUENCY RESOLVED IMAGING SYSTEM

(75) Inventor: Joshua Noel Hogan, Los Altos, CA (US)

(73) Assignee: FP Technology, Mountain View, CA (US)

( * ) Notice: Subject to any disclaimer, the term of this patent is extended or adjusted under 35 U.S.C. 154(b) by 1528 days.

(21) Appl. No.: 11/048,694

(22) Filed: Jan. 31, 2005

(65) Prior Publication Data

US 2006/0058608 A1 Mar. 16, 2006

Related U.S. Application Data

(63) Continuation-in-part of application No. 11/025,698, filed on Dec. 29, 2004, now Pat. No. 7,526,329.

(60) Provisional application No. 60/602,913, filed on Aug. 19, 2004.

(51) Int. Cl.
*A61B 5/1455* (2006.01)
*A61B 6/00* (2006.01)

(52) U.S. Cl. .................. 600/316; 600/310; 600/473; 600/476

(58) Field of Classification Search .......... 600/310, 600/316, 473, 476, 322; 356/450, 451, 456, 356/477, 479
See application file for complete search history.

(56) References Cited

U.S. PATENT DOCUMENTS

| 6,198,540 B1 | 3/2004 | Ueda et al. |
| 6,725,073 B1 * | 4/2004 | Motamedi et al. ........... 600/316 |
| 6,728,571 B1 * | 4/2004 | Barbato ...................... 600/407 |
| 6,775,007 B2 | 8/2004 | Izatt et al. |

* cited by examiner

*Primary Examiner*—Eric F Winakur

(57) ABSTRACT

A non-invasive imaging and analysis system suitable for non-invasive imaging and analysis of defects or malignant aspects of targets such as cancer in skin or human tissue and suitable for measuring concentrations of specific components, such as blood glucose concentration includes an optical processing system which generates a probe and composite reference beam. The system also includes a means for applying the probe beam to the target to be analyzed and modulates at least some of the components of the composite reference beam such that signals with different frequency content are generated. The system combines a scattered portion of the probe beam and the composite beam interferometrically to simultaneously acquire information from multiple depths within a target. It further includes electronic control and processing systems.

52 Claims, 4 Drawing Sheets

FREQUENCY RESOLVED IMAGING SYSTEM

CROSS REFERENCES TO RELATED APPLICATIONS

This application, is a continuation in part of U.S. utility application Ser. No. 11/025,698 filed on Dec. 29, 2004 now U.S. Pat. No. 7,526,329 titled "Multiple reference non-invasive analysis system", the contents of which are incorporated by reference as if fully set forth herein. This application, claims priority from provisional application Ser. No. 60/602,913 filed on Aug. 19, 2004 titled "Multiple reference non-invasive analysis system". This application also relates to U.S. utility application Ser. No. 10/949,917 filed on Sep. 25, 2004 titled "Compact non-invasive analysis system", the contents of which are incorporated by reference as if fully set forth herein.

FIELD OF THE INVENTION

The invention relates to non-invasive optical imaging and analysis of targets and in particular to non-invasive analysis of defects or malignant aspects of targets such as cancer in skin or human tissue. This invention also relates to quantitative analysis of concentrations of specific components or analytes in a target. Such analytes include metabolites, such as glucose.

BACKGROUND OF THE INVENTION

Non-invasive imaging and analysis is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process.

In the particular case of non-invasive in-vivo imaging and analysis of human tissue, it is desirable to replace a conventional physical biopsies in favor of non-invasive optical biopsy. In the case of measurement of blood glucose levels in diabetic patients, it is highly desirable to measure the blood glucose level frequently and accurately to provide appropriate treatment of the diabetic condition as absence of appropriate treatment can lead to potentially fatal health issues, including kidney failure, heart disease or stroke. A non-invasive method would avoid the pain and risk of infection and provide an opportunity for frequent or continuous measurement.

An existing non-invasive imaging and analysis technology, optical coherence tomography (OCT), using a super-luminescent diode (SLD) as the optical source, is being used to image and analyze tissue. The SLD output beam has a broad bandwidth and short coherence length. The technique involves splitting the output beam into a probe and reference beam. The probe beam is applied to the system to be analyzed (the target). Light scattered back from the target is combined with the reference beam to form the measurement signal. Because of the short coherence length only light that is scattered from a depth within the target such that the total optical path lengths of the probe and reference are equal combine interferometrically. Thus the interferometric signal provides a measurement of the scattering value at a particular depth within the target. By varying the length of the reference path length, a measurement of the scattering values at various depths can be measured and thus the scattering value as a function of depth can be measured, providing image or analytic information.

In conventional OCT systems depth scanning is achieved by modifying the relative optical path length of the reference path and the probe path. The relative path length is modified by such techniques as electromechanical based technologies, such as galvanometers or moving coils actuators, rapid scanning optical delay lines and rotating polygons. All of these techniques involve moving parts that have to move a substantial distance, which have limited scan speeds and present significant alignment and associated signal to noise ratio related problems.

Motion occurring within the duration of a scan can cause significant problems in correct signal detection. If motion occurs within a scan duration, motion related artifacts will be indistinguishable from real signal information in the detected signal, leading to an inaccurate measurement. Long physical scans, for larger signal differentiation or locating reference areas, increase the severity of motion artifacts. Problematic motion can also include variation of the orientation of the target surface (skin) where small variations can have significant effects on measured scattering intensities.

Non-moving part solutions, include acousto-optic scanning, can be high speed, however such solutions are costly, bulky and have significant thermal control and associated thermal signal to noise ratio related problems. Optical fiber based OCT systems also use piezo electric fiber stretchers. These, however, have polarization rotation related signal to noise ratio problems and also are physically bulky, are expensive, require relatively high voltage control systems and also have the motion related issues.

These aspects cause conventional OCT systems to have significant undesirable signal to noise characteristics and present problems in practical implementations with sufficient accuracy, compactness and robustness for commercially viable and accurate imaging and analysis devices. Therefore there is an unmet need for commercially viable, compact, robust, non-invasive imaging and analysis technology and device with sufficient accuracy, precision and repeatability to image or analyze targets or to measure analyte concentrations, and in particular to image and analyze human tissue.

SUMMARY OF THE INVENTION

The invention provides a method, apparatus and system for a non-invasive imaging and analysis of targets and in particular to non-invasive analysis of defects or malignant aspects of targets such as cancer in skin or human tissue. This invention also relates to quantitative analysis of concentrations of specific components or analytes in a target. Such analytes include metabolites, such as glucose. The invention includes a radiation source and a radiation signal processing system which provides a probe and a composite reference beam. It also includes a means for applying the probe beam to the target to be analyzed, recombines the scattered probe beam and the composite reference beam interferometrically and simultaneously acquires information from different locations within the target. It further includes electronic control and processing systems.

DETAILED DESCRIPTION OF THE INVENTION

Figure 1:
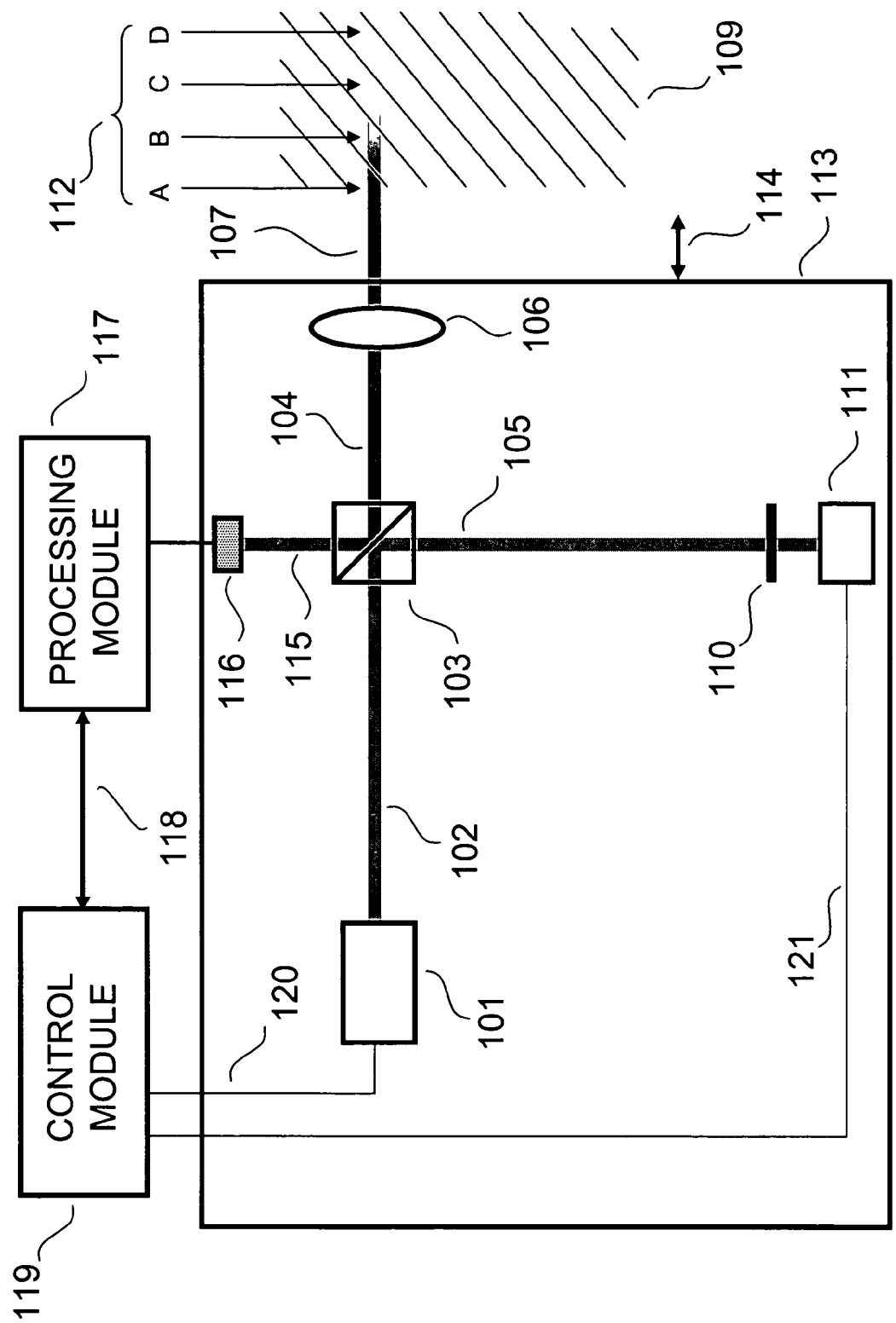
FIG. 1 is an illustration of the non-invasive imaging and analysis system according to the invention.

Conventional optical coherence tomography is based on splitting the output of a broadband optical source into a probe beam and a reference beam and of varying the optical path length of the reference beam to scan the target. This approach has problems and limitations including problems and limitations related to motion occurring within the duration of a scan.

The present invention is a novel interferometric approach which addresses these problems and limitations by simultaneously acquiring multiple meaningful interferometric signals from multiple depths within the target, thus avoiding relative motion artifacts. With the present invention the interferometric signals from the different depths within the target have different frequency content and thereby can be distinguished from each other and separated by electronic filtering or digital signal processing thereby achieving a scan of a target.

The invention involves generating composite reference radiation (or a composite reference beam) consisting of multiple component radiation (or component reference beams) each having a different path length. In addition to having different path lengths, the components of the composite reference radiation are also effectively modulated at different frequencies by imposing different frequency content on the different components of the composite reference radiation.

This enables forming a composite interferometric signal by combining the composite reference radiation with a portion of probe radiation scattered by a target of interest. The composite interferometric signal can be processed to provide information corresponding to different components of the composite reference. This enables a compact processing system which can simultaneously acquire and analyze information from different depths within a target thereby scanning the target in a manner that avoids undesirable motion related artifacts.

For purposes of this invention, imposing different frequency content on different components of reference radiation to form composite reference radiation includes any method, apparatus or system that modifies reference radiation such that when combined with a portion of probe radiation or scattered probe radiation, an composite interference signal is generated that has interference components that correspond to different components of the reference radiation and these different interference components have different frequency content.

In a preferred embodiment the radiation is optical radiation and referred to as a beam, the reference radiation is referred to as a reference beam and the probe radiation as a probe beam. The component reference beams are generated by a combination of a first partially reflective element and a second reflective element whose position is varied to change the path length of the component reference beams. The multiple component reference beams are generated by multiple reflections between the first partially reflective element and the second reflective element.

The range of scan of different component reference beams increases with the multiplicity of reflections (also referred to as the multi pass order, N) enabling a significantly larger scan range at deeper levels within the target. Deeper scans may also overlap allowing improved performance. The deeper larger scans occur at the same repetition rate as the smaller scans and therefore have no increased sensitivity to motion. A smaller first order scan enables higher speed scanning while still generating larger scan ranges at deeper (multiple reflection) levels.

In addition to having different magnitude scan ranges, the scans due to different multiple reflections generate interferometric signal with different frequency content enabling the interferometric information from the different component reference beams corresponding to different depth scans to be separated by electronic processing. This enables a compact processing system which can simultaneously acquire and analyze information from different depths within a target and thereby avoid undesirable motion related artifacts.

A preferred embodiment of this invention is illustrated in and described with reference to FIG. 1 where a non-invasive optical analysis system is depicted. The analysis system includes an optical processing system that generates a probe beam and a reference beam from a broadband optical source 101 such as a super-luminescent diode or a mode-locked laser, whose collimated output 102 consists of a broad band, discrete or continuous set of wavelengths.

The output beam 102, is passed through a beam splitter 103, to form a probe beam 104 and a reference beam 105 (which also becomes the composite reference beam on its return path). The probe beam 104 passes through an optional focusing lens 106. The focusing probe beam 107 is applied to the target 109 of interest.

At least part of the radiation of the beam applied to the target is scattered back and captured by the lens 106 to form captured scattered probe radiation. Scattering occurs because of discontinuities, such as changes of refractive index or changes in reflective properties, in the target. The captured scattered probe radiation passes through the lens 106 back to the beam splitter 103.

The reference beam 105 is partially reflected by the partial reflective element 110. A portion of the reference beam is also transmitted through the partial reflective element 110 which is then reflected by the modulating reflective element 111 to form a once modulated reference beam. A portion of the once modulated reference beam is transmitted through the partial reflective element 110 to form a component of the composite reference beam 105. The modulation imposes frequency content on the component reference beam.

A portion of the once modulated reference beam is also reflected by the partial reflective element 110 and is again reflected and further modulated by the modulating reflective element 111. A portion of this twice modulated reference beam is then transmitted through the partial reflective element 110 to form another component of the composite reference beam 105 with higher frequency content imposed on this second component reference beam and a portion also is reflected by the partial reflective element 110 to form further components of the composite reference beam that are multiple times modulated reference beams each with higher frequency content imposed on the components.

In this manner a composite reference beam 105 is generated that has multiple interferometrically significant components that correspond to depth locations within the target 109, a subset of which depths are indicated by the set of arrows 112 labeled B, C and D. The depth location indicated by the arrow labeled "A" corresponds to the partially reflective element 110 and would have a corresponding interference signal with a frequency content determined by the relative motion between the target 109 and the micro-bench 113 along the direction indicated by 114.

This relative motion could be zero in the case where there is no relative motion between the target and micro-bench. Alternatively this interferometric signal can be measured and used to remove or compensate for similar motion related aspects of other interferometric signals. Furthermore, successive motion related measurements can be used to predict and pre-compensate for motion. Also controlled motion and relative position could be generated by pressing the target against a deformable element of the optical analysis system.

Depth location "B" corresponds to the modulating reflective element 111 (single pass or order "1" pass or first order) and would have a corresponding interference signal with a frequency content determined by the modulating frequency. Depth location "C" corresponds to a double pass (or order "2" multiple pass) between the modulating reflective element 111 and the partially reflective element 110 and would have a corresponding interference signal with a frequency content twice that of the interference signal corresponding to depth location "B".

Depth location "D" corresponds to a triple pass (third order or order 3 pass) between the modulating reflective element 111 and the partially reflective element 110 and would have a corresponding interference signal with a frequency content three times that of the interference signal corresponding to depth location "B". Interference signals corresponding to higher order multiple passes with correspondingly higher frequencies could also exist. In general, the resulting composite interference signal will have multiple interference components which contain simultaneous information from multiple depth locations.

There is a decrease in the intensity of the reference beam components corresponding to higher order multiple passes. The amount of this decrease in intensity depends on the partially reflecting element. For example, if the partial reflective element reflects 50% and transmits 50% of the reference beam, then the reference beam component from the partially reflective element 110 (corresponding to A) will have a relative intensity of approximately 50% ; the reference beam component from a single pass to the modulating reflective element 111 (corresponding to B) will have a relative intensity of approximately 25%. Partial reflection other than 50% can be used. These relative intensities are approximate because of absorption and noise effects.

Similarly, the reference beam component from a double pass to the modulating reflective element 111 (corresponding to C) will have a relative intensity of 12.5%; the reference beam component from a triple pass to the modulating reflective element 111 (corresponding to D) will have a relative intensity of 6.25% ; and so on. Typically, the captured scattered signal from the target will be of low intensity and having reference beam components with different relative intensities will not be significant as they will likely exceed the intensity of the scattered signal.

The reflective element 111 includes a modulating element and is also referred to as a modulating reflecting element. The modulating reflective element affects the different component reference beams by different magnitudes corresponding to different path lengths due to reflecting a different number of times. This causes different component reference beams to be modulated by different magnitudes. This causes the resulting interferometric signals corresponding to different component reference beams and thereby to different depths (within the target) to have different frequency components which allows the interferometric information from the different depths to be separated by electronic filtering.

This provides a mechanism for simultaneously analyzing information from different depths within the target, thereby avoiding motion artifacts. The frequencies of the different interference signals are all determined by the single pass piezo scan multiplied by the number of reflections (or the order of the multiple pass, N). This mechanism also means the different frequencies are all harmonically related which facilitates separating them by digital signal processing or analog filtering.

At least a part of the modulated reflected component reference beams are re-combined after they pass through the partially reflective element 110 towards the beam-splitter 103 to form a re-combined reference beam which returns along the path of the reference beam 105 and is referred to as a composite reference beam. The reflected re-combined reference beam, or composite reference beam, is combined interferometrically with the captured scattered probe radiation in the beam splitter 103.

Although typically referred to as a beam splitter the optical element 103 also operates as an optical combining element, in that it is in this element that reflected re-combined reference beam and captured scattered probe radiation combine interferometrically. The resulting composite interference signal 115 is detected by the opto-electronic detector 116 to form a composite electronic signal.

A meaningful interferometric signal only occurs with interaction between the reference beam and light scattered from a distance within the target such that the total optical path lengths of both reference and probe paths are equal or equal within the coherence length of the optical beam. In this preferred embodiment simultaneous information from multiple different depth locations is simultaneously acquired and analyzed.

The preferred embodiment also includes an electronic processing module, 117, which interacts with an electronic control module 119 by means of electronic signals 118. The control module 119 provides timing signals, included in signals 118, to provide the electronic processing module 117 with timing signals to assist the processing module with filtering and processing the detected composite interferometric signals. The control module 119 also generates control and drive signals for the system, including signals 120 to control and drive the optical source and signals 121 which modulates the modulating reflective element 111.

Modulation can be accomplished by phase modulating the component reference beams by means of the modulating reflective element 111, which in this case would be a reflective phase modulator. Applying a repetitive phase modulation of nominal magnitude 90 degrees in single pass, (180 degrees double pass) or greater generates a detectable interferometric signal related to the frequency of the repetitive phase modulation.

In the preferred embodiment, the modulating reflective element 111 involves a length modifying device, such as piezo-electric device, which enables performing scans within the target. By modifying the length of the reference path to the reflective element 111 the different multiple pass component reference beams will have increasingly larger magnitude scans. For example, if the translation range of the reflective element 111 is 20 microns, the range within the target corresponding to the interferometric signal of the single pass, i.e. at location "B" of 112, would be 20 microns. This could be regarded as a 20 micron scan, however if the depth resolution of the SLD is less than this there is little meaningful scanning capability.

The range within the target corresponding to the interferometric signal of the tenth multiple pass however would be 200 microns and would represent a significant scanning range. This amplification of scanning range by multiple passes of the reference beam provides an effective method of generating a significant scanning range, without large magnitude translations of the reflective element 111.

Figure 2:
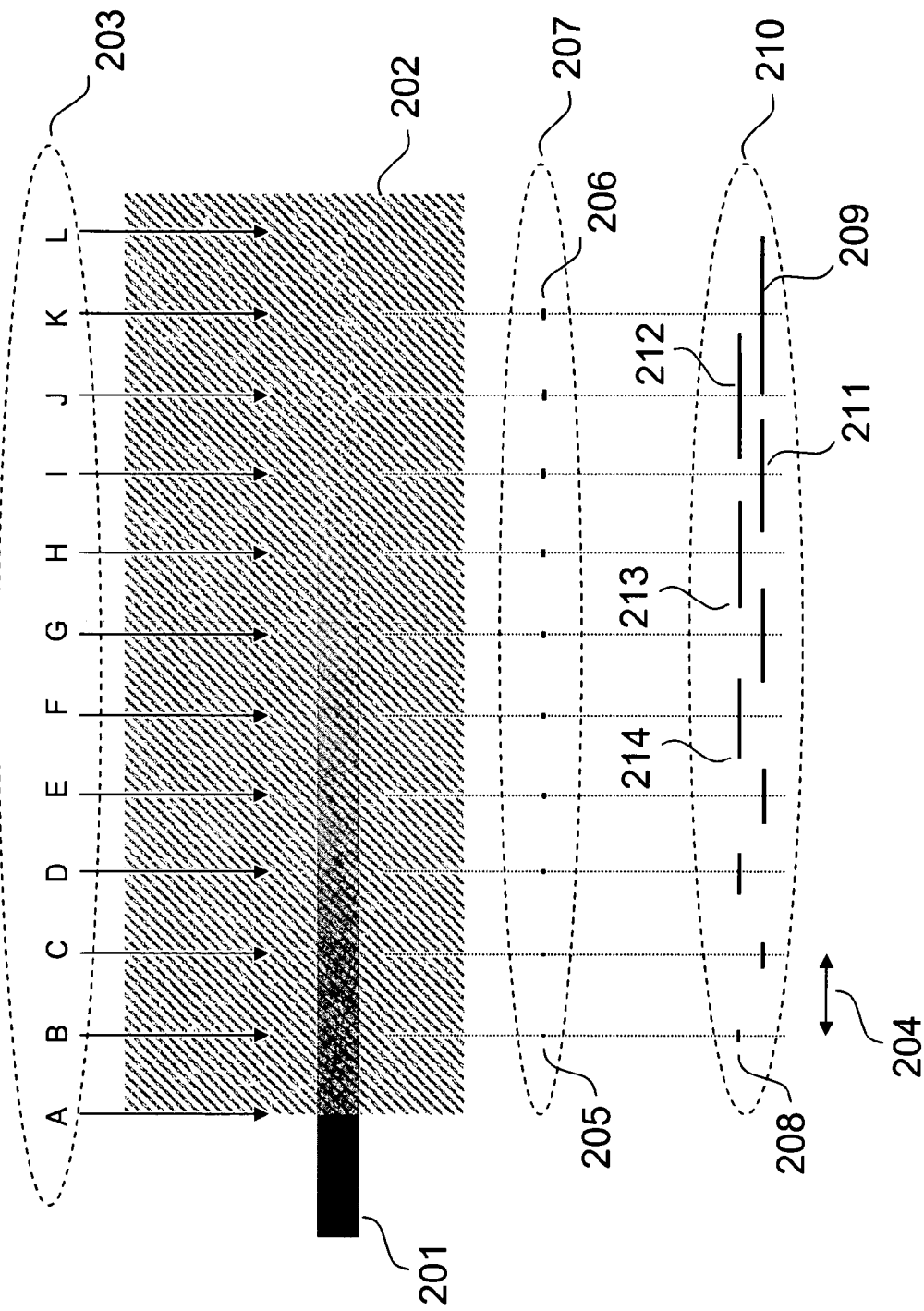
FIG. 2 is an illustration of scanned regions within a target.

This amplification of scanning magnitude is illustrated in FIG. 2 where the probe beam 201 is applied to the target 202. Different depths within the target are indicated by the set of arrows labeled A, B, C, D, F, F, G, H, I, J, L enclosed in the dashed oval 203. These arrows indicate depths within the target 202 separated by a distance determined by the separation between the partially reflective element 110 and the reflective element 111 (of FIG. 1) modified by refractive indices and indicated by the double arrow depth separation 204.

For example, the separation between the partially reflective element 110 and the reflective element 111 (of FIG. 1) determines a depth separation 204 of magnitude 100 microns. If the single pass piezo scanning range is 2 microns, indicated by the dot 205, the scanning range of the tenth pass (or tenth of the multiple reflection set) will be 20 microns, indicated by the line 206. The complete set of gradually increasing scan ranges are indicated by the set of marks, systematically expanding from the dot 205 to the line 206, enclosed by the dashed oval 207 and extend over a region of the target in excess of 1 mm.

With an SLD with a bandwidth of several tens of nanometers corresponding to a depth resolution of the order of 40 microns, scan ranges of the order of 2 to 20 microns are below the resolution of the system and therefore may be regarded as enabling acquiring simultaneous information from a set of depths within the target (rather than scanning).

If, however, the single pass piezo scanning range is, for example, 20 microns, indicated by the line 208, the scanning range of the tenth pass (or tenth of the multiple reflection set) will be 200 microns, indicated by the line 209, which is a substantial scanning range. The complete set of gradually increasing scan ranges are indicated by the set of marks, expanding from the line 208 to the line 209, enclosed by the dashed oval 210. The vertical offset of alternate lines within the set is for clarity purposes only and has no other significance. All of these lines indicate locations in the target intersected by the horizontal probe signal 201.

The higher order scans overlap adjacent scans, providing a method for achieving a complete scan of a region. For example the scan 211 corresponding to the region indicated by the arrow labeled "I" of the set 203 clearly overlaps the two adjacent scans 212 and 213. In the example of scans enclosed in the oval 210 completely scans the region of the target from the front (left end or less deep portion) of scan 214 to as deep as a detectable scattered signal emerges from and a significant component reference signal being available.

Thus the region defined by the scan 214 to at least scan 219 can be completely scanned making this technique suitable for imaging as well as analysis. Some portions of deeper regions are scanned by at least two overlapping scans which provides a mechanism for correlating scans to normalize and/or reduce noise in scans. The fact that the multiple scans, covering a complete region, are acquired simultaneously improves the speed with which the complete region can be imaged or analyzed, thus reducing sensitivity to motion artifacts.

The deeper scans span regions of increasing magnitude, but in the same period of time, and therefore generate interferometric signals with different and increasing frequency content. This enables the multiple interferometric signals to be separated by processing in the electronic domain, which allows the simultaneous acquisition of scanned information from multiple depths.

Scans performed by using a piezo device are typically operated with a linear scan speed in the center region and slows to a stop at the extremes of the scan, often with a sine wave form characteristic. This may require only using a center region of the scan. The useful center region can be extended by electronic processing to compensate for or to reduce non-linear aspects. The preferred embodiment employs a piezo-electric device, however, other length modifying or modulating mechanisms, such as electro-mechanical or acousto-optic, can be used.

Optical processing systems, such as described above, can be fabricated on a compact micro-bench, such as a silicon micro-bench. This is illustrated in FIG. 1 by the boundary or box 113 which illustrates the boundary of a rigid micro-bench. All components within the boundary or box 113 can be mounted on such a micro-bench. By varying the distance between the micro-bench 113 and the target 109, the distance into the target from which the meaningful interferometric signals originate is varied along a line determined by the probe beam. Various methods of translating the micro-bench are illustrated and described in the patent application Ser. No. 10/949,917 referenced by and incorporated into this application.

Relative motion between the micro-bench 113 and the target 109 will generate an interferometric signal that will effectively be added to the other interferometric signals. This signal may be detected and its value enhanced by arranging for the surface of the target to nominally correspond to the initial reflection from the partially reflective element 110 and is indicated by the arrow labeled "A" at the front of the target in both FIGS. 1 and 2.

This interferometric signal may be used to determine the relative motion of the target and micro-bench and to eliminate the motion by a conventional motion controlled feed-back system or to compensate for the measured motion by appropriately modifying the other interferometric signals. Predictive techniques may also be applied by processing and correlating successive motion measurements to reduce relative motion.

The interferometric signals that do not have sufficient scan range to cover a complete region within the target may be used for purposes other than imaging. For example in depth scans indicated by the label "A" and the scans indicated by the dashed oval 210 of FIG. 2, and the arrows labeled "B", "C", "D" and "E" represent scans that leave regions un-scanned. The information acquired from these interferometric signals may be used for multi-dimension positioning or aligning the optical system micro-bench 113 with respect to the target 109.

This may be accomplished by comparing the acquired information with known registration marks. Such marks include, but are not limited to: surface marks such as tattoos, freckles or blemishes; depth structures such as variations in the epidermis, other physiological aspects or artificial embedded structures. The information may also be used to measure other characteristics which include, but is not limited to, the degree of compression in the target or the alignment of the probe signal with respect to the normal to the surface of the target.

The depth separation 204 of the multiple scans is determined by the separation between the partially reflective element 110 and the reflective element 111. The magnitude of the scans is determined by the magnitude of the single pass scan 205 or 208 and the number or order of passes, N. The scans that overlap and, therefore the region that can be completely scanned, is determined by both the depth separation 204 and the magnitude of the single pass piezo scan and the order of passes, N.

The magnitudes of the depth separation and single pass scan can be varied to suit particular applications. These magnitudes can be fixed for a particular design, or one or both magnitudes can be varied dynamically during operation. For example, a depth separation of 100 microns and a small single pass scan such as 2 microns enables simultaneous analyzing small segments over a range of 1 mm (with ten multi pass reflections or N of 10) within the target.

By varying the depth separation continuously from 100 microns to 50 microns (by, for example, controlling an offset of the piezo device) multiple offset sets of simultaneously acquired information can be accumulated thus effectively providing a complete scan of at least the deeper 0.5 mm of the 1 mm of the target being analyzed. An advantage of using a small single pass scan is that it can be accomplished at very high speed which makes each simultaneously acquired set of information less sensitive to motion artifacts.

Alternatively the micro bench 113 could be translated with respect to the target 109 to acquire a complete scan of the region of interest within the target. Insensitivity to motion artifacts is achieved again by the fact that each set of simultaneously acquired information. Other possible designs include, but are not limited to, varying any combination of depth separation, single pass scan magnitude and position of the micro-bench with respect to the target. Suitable combinations can be designed to optimize scanning of a region or regions of interest within a target and may be dynamically reconfigured.

The ability of this technique to acquire simultaneous information over, for example, a range of 1 mm of the target by using a 2 micron single pass scan and 10 passes provides an effective increase in scanning speed by a factor of the order of 500. The resulting scan may be regarded as a sampling scan as it does not necessarily provide continuous information over the full 1 mm range. This, however, provides significant insensitivity to motion artifacts.

Using a 20 micron single pass scan range, that enables complete scanning of regions of the target provides an effective increase in scanning speed by a factor of the order of 50 which also gives significantly improved insensitivity to motion artifacts. Alternatively, a 2 micron single pass scan combined with translating the micro-bench 100 microns could provide a complete scan of the 1 mm region of the target. Also practical scan speeds typically increase in a non-linear manner that enables even higher speeds.

The multiple sets of simultaneously acquired information (which are each insensitive to motion artifacts) may be correlated with each other using conventional image reconstruction techniques to generate a complete scan that has reduced sensitivity to motion. The combination of high speed scanning, simultaneous acquisition of information from multiple regions, overlap of adjacent scans in a region of interest within the target, registration techniques, and image reconstruction techniques enables a powerful novel imaging and analysis technology. The optional focusing lens 106 of FIG. 1 can be selected to maximize performance at the region of interest.

Having sets of simultaneously acquired information is particularly insensitive to motion if the characteristic being analyzed is dependent on the relationship between signals from different depths and not critically dependent on the actual depth values. For example information about the concentration of analytes, such as the concentration of glucose in tissue, can be determined from relationship between signals from different depths without knowing the actual depth values. Effects of motion, however, are a serious source of measurement disruptive noise.

The relative intensity of the different component reference beams decreases with an increasing number of multiple reflections. The less intense component reference beams correspond to deeper regions within the target. The decrease in intensity is substantially linear with the order of the multiple reflection, decreasing linearly corresponding to deeper regions within the target. The order, N, of the multiple reflections would be 1 for the single pass component reference, 2 for a double pass reflection, 3 for a triple pass reflection, etc.

The relative intensity of the scattered signal typically decreases linearly with the log (logarithm) of depth into the target, therefore the linearly decreasing component reference beam will typically be of larger magnitude than its corresponding scattered signal. The frequency content of the interferometric signals also increase linearly with the order of the multiple reflection N. This provides an opportunity to optimize signal detection by using an amplifier whose gain increases logarithmically with frequency.

Figure 3:
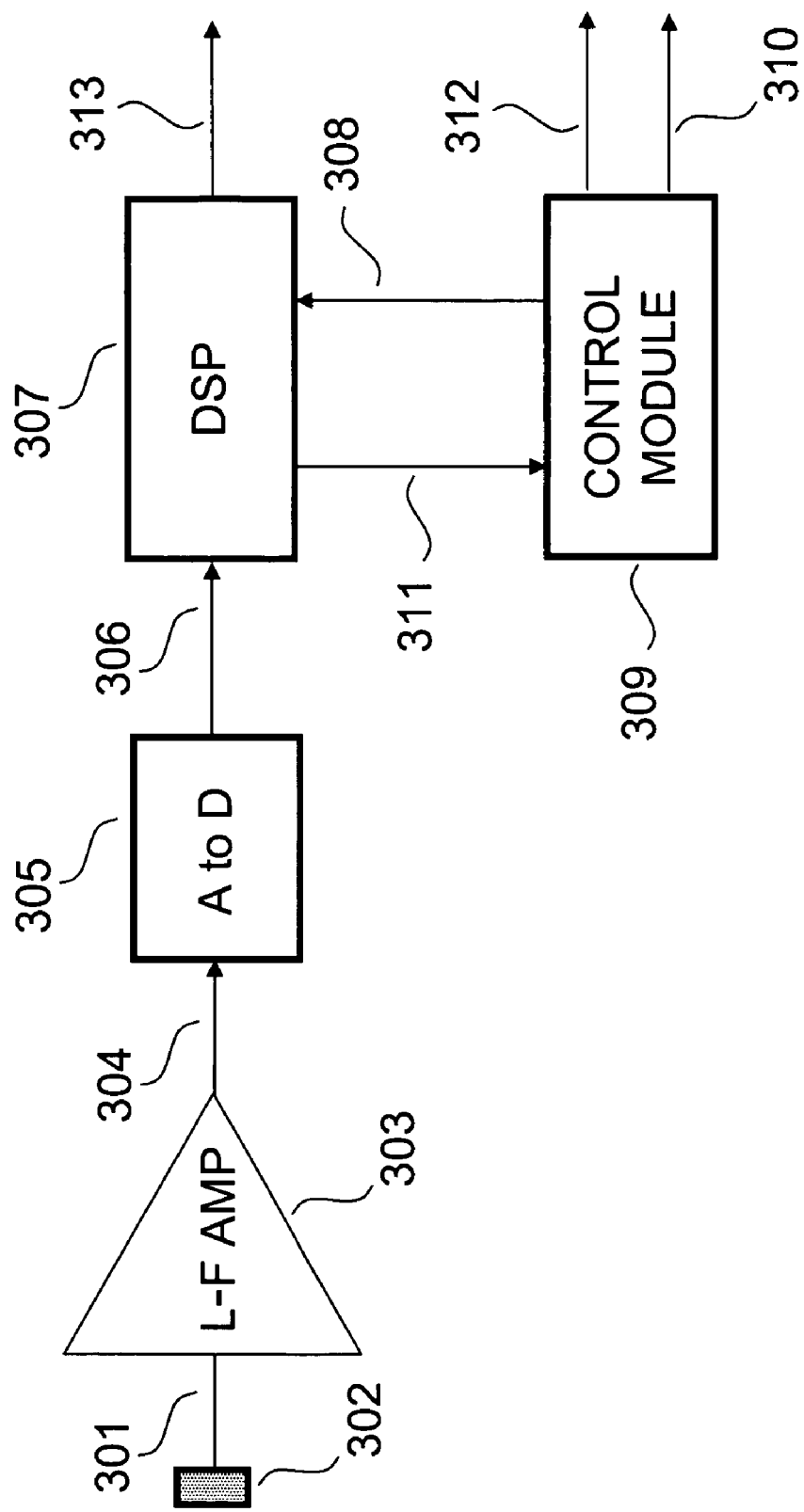
FIG. 3 is an illustration of amplifying, processing and control aspects of the invention.

Conventional Log-Amps (logarithmic amplifiers have gain that is dependent on the amplitude of the input signal. A Log-Amp with gain dependent on the frequency of the input signal enhances the signal detection capability of signals from different depths within the target. A Log-Amp with gain dependent on time and repeating with a time period matching the repetitive period of the modulating (length varying) signal can enhance the signal detection capability of signals from different locations within individual continuous segments scans within the target. A This is illustrated in FIG. 3 where the output 301 of the opto-electronic detector 302 is applied to an amplifier 303 labeled "L-F AMP", which may include a conventional preamplifier, amplifies the detected composite interferometric signal with a gain that is proportional to the log of the frequency, thereby preferentially amplifying the weaker signals scattered from deeper within the target. This provides a mechanism for optimizing the detected signal for processing, which in the preferred embodiment includes digitizing the amplified signal 304 by an analog to digital converter 305 labeled "A to D".

The digital output 306 of the A to D 305 is applied to a digital signal processor 307 labeled "DSP". The DSP 307 processes the amplified digitized detected signal. It also receives timing information 308 from the control module 309 regarding the piezo drive signal 310 (corresponding to 120 of FIG. 1). The DSP 307 derives clock and filtering information from the timing information and the frequency content of the detected signal which enables a feedback scheme that modifies the piezo drive signal to set or center the desired frequency values. An advantage of this embodiment is that the frequencies of the different component interference signals are automatically harmonically related or have aspects that are harmonically related.

The DSP 307 filters and analyses the detected signal and derives depth related information. It provides information 311 which includes depth related information that may entail surface and depth registration information to the control module 309. The control module 309 uses this information to modify the piezo modulating signal 310 which adjusts the magnitude of the single pass scan (205 or 208 of FIG. 2), to optionally also modify the depth separation (204 of FIG. 2) and optionally to also modify other positioning aspects such as the translation or other positioning of the micro-bench (113 of FIG. 1).

In this manner the system optimizes scanning of the region or regions of interest within the target. The signal to noise ratio of this novel scanning technique is automatically enhanced by the fact that multiple reference beams corresponding to multiple depths are simultaneously acquired (rather than sequentially as in a conventional OCT system) and thus a scan achieved. The degree of enhancement is related to the number of distinct interference signals separated out by the DSP 307 which is related to the usable component reference beams.

The signal to noise ratio of this novel scanning technique may also be increased by modulating the optical source by a control signal 312 (corresponding to 121 of FIG. 1). The optical source is turned off during the extreme portions of the piezo scan as the frequencies of the associated interference signals are decreasing rapidly and of less analytic value. The optical source may be turned on and off in a smooth manner such that it peaks coincident with the duration of maximum frequency.

Matching the rise and fall of the intensity of the optical signal to the magnitude of the displacement of the piezo device allows equalizing the energy in the different cycles of the interference signals, thus enhancing the detected signal. Pulsing the optical source also enables enhancing the signal to noise ratio by having a higher peak power with the same average power. Average power (rather than peak power) may be limited by safety considerations.

Pulsing the optical source also provides an opportunity to illuminate the target with a second light source for visual or automatic alignment of the micro-bench with registration marks. Pulsing the second optical source on when the main broadband optical source is off or of low intensity avoids interference with the main broadband optical source. Detecting reflected or scattered signals from both sources with the same detector facilitates alignment.

With appropriate positioning of the micro-bench and alignment of scanning with the region or regions of interest within the target, the DSP 307 of FIG. 3 the generates interference related digital data 313 which contains desired information. The specific data generated from the interference signals depends on the specific imaging or analysis application. The data 313 is further processed, stored or transmitted also depending on the particular application.

The interference signal corresponding to region "A" in the target 109 is determined by the relative motion between the target 109 and the beam-splitter 103. This relative motion may be negligible in the case of a stationary target. In an alternative embodiment the target may be vibrated in a controlled manner. In this embodiment a vibration may applied to the target by means of an oscillating or vibrating device that is applied to the target. A flexible or deformable element or index matching element can facilitate having the surface region "A" of the target vibrate and reduce the scattering at this interface.

Many alternative methods of imposing an oscillating relative motion between the target and the beam-splitter. For example a conventional voice coil or a piezo device could be used to impart a small vibration to the target. The frequency and amplitude of the vibration can be selected so that the resulting interference signal corresponding to region "A" does not significantly interfere with the frequency of the interference signals corresponding to other regions including regions B, C and D etc. Alternatively, particularly in the case where the target is human tissue and the target, such as a region of a finger, can be readily moved, then relative motion between the target and the beam-splitter could be imposed by moving the target.

Analyzing scattering information of targets can provide information relating to generating an image of the scanned region or to measuring the concentration of components within the target. For example, a suspected cancerous region of tissue can be imaged and analyzed. In another example, the scattering coefficient of tissue can be analyzed to determine the concentration of components or analytes, such as glucose, within the tissue. The present invention provides a method of imaging or analyzing a target in a manner that has significant insensitivity to the blurring or noisy aspects of motion.

Depending on the application and the mode of implementation a scan of the target may consist of information from a simultaneously acquired set of signals. Each signal may range over a continuous region of the target. If the range is small compared to the optical resolution of the source radiation, then the acquired information is suitable for analyzing the target or registering (aligning) the target with respect to the probe beam and the acquired scan is herein referred to as a sampling scan.

If the range exceeds the optical resolution of the source radiation, then the acquired information is suitable for imaging, analysis and registration and is herein referred to as a segmented scan. The range of some segments may be large enough to form a continuous scan of a region of interest and is herein referred to as a continuous scan. If the range is large enough that adjacent imaging scans overlap, then the acquired information is suitable for continuous imaging, analysis and registration and the acquired scan is referred to as a composite continuous scan.

A simultaneously acquired set of signals may include all types of scans and different ones may be used for different purposes. For example, the less deep signals corresponding to regions labeled "B", "C" and "D" of the set of scan ranges 210 of FIG. 2 may be used for registration purposes while those labeled "G", "H", "I", "J" and "K" are overlapping and could be used to acquire a composite continuous scan over the range spanned by "G" through "H" which could be used for imaging or analysis.

Multiple overlapping continuous segments can be combined to generate a composite continuous scan using conventional techniques that include, but are not limited to, correlation, registration, motion compensation, correction for expansion or compression, noise reduction. Multiple sets of sampling, segmented, continuous, or composite continuous scans can also be correlated and processed to generate enhanced (or noise reduced) image and analysis information. These and other imaging and analysis techniques are herein referred to as image reconstruction techniques.

Because multiple resultant interferometric information exists within the same interferometric signal, an interferometric signal may include more than one interferometric signals. For purposes of this application interferometric signal, composite interferometric signal and interferometric signals may be used interchangeably. Also for purposes of this application beam, optical beam and radiation may be used interchangeably. The preferred embodiment is described with respect to an optical analysis system, however, the invention includes systems using other forms of radiation including, but not limited to, acoustic radiation and all electro-magnetic radiation.

For purposes of this invention, the term path length includes optical path length and in general a path length that may be physically modified by one or more refractive index. For purposes of this invention scanning includes scanning for imaging purposes and scanning for analysis purposes.

It is understood that the above description is intended to be illustrative and not restrictive. Many of the features have functional equivalents that are intended to be included in the invention as being taught. Many variations and combinations of the above embodiments are possible, for example, various combinations of length modulators can be used, including but not limited to piezo-ceramic modulators, piezo-electric modulators, quartz crystals, phase modulators and electro mechanical modulators. Mechanically amplified piezo-electric actuators can be used to increase length changes or to translate the optical system on a micro-bench. In some embodiments the relative optical path lengths of reference beams could be systematically varied to vary the relative locations from which information is obtained simultaneously.

In general, various length modulators (or translation elements)can be used to determine and optimize the extent and region within the target that is scanned for registration, for a sampling scan, for a continuous scan, for a composite continuous scan, and to vary the relative displacement and relative motion of the target and the analyzing system. For purposes of this invention, such length modulators and phase modulators are referred to as translation elements and may be used to optimize the above aspects of scans for a particular application.

Figures 4, 4A, 4B, 4C:
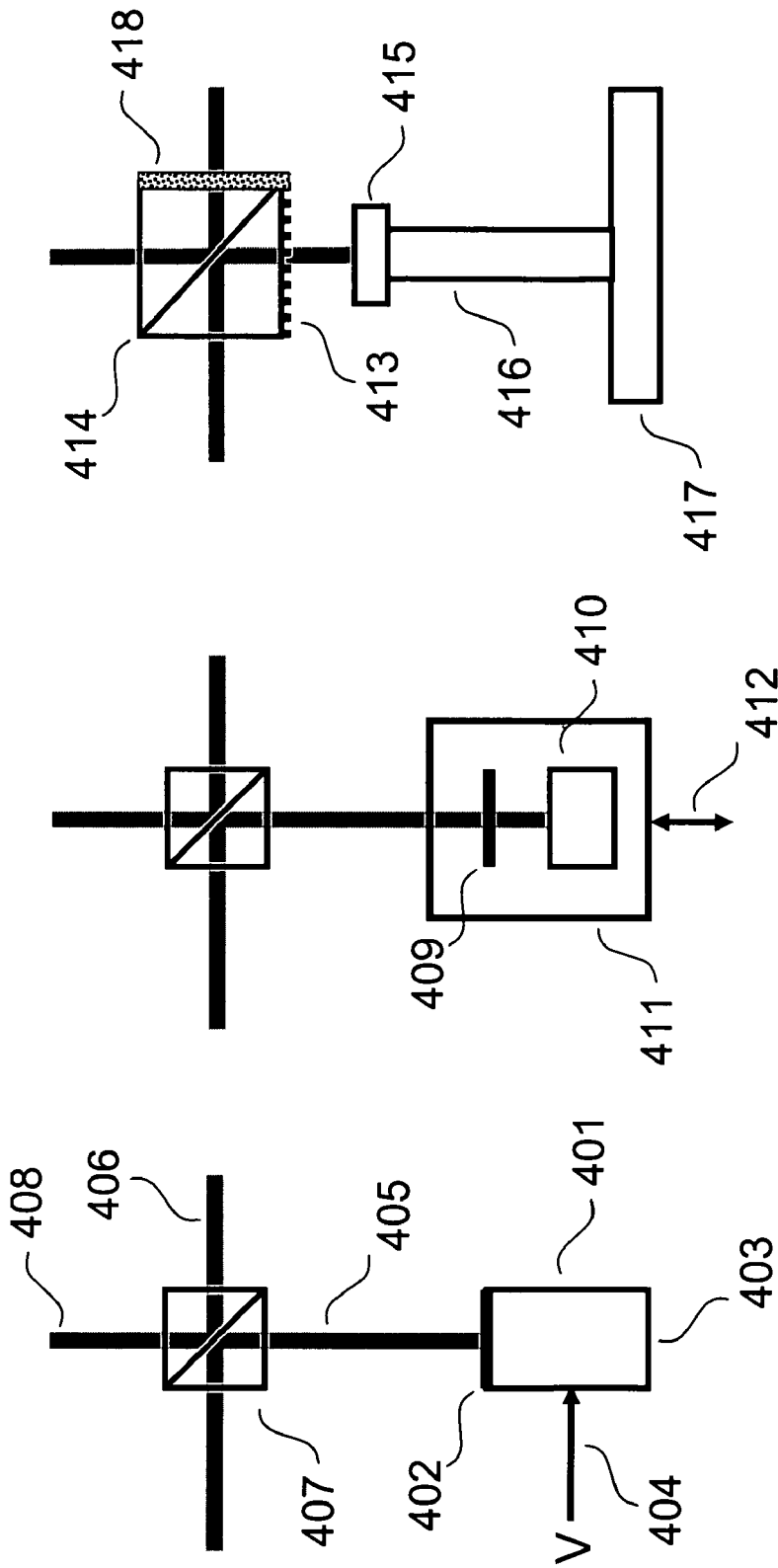
FIG. 4 illustrates various examples possible of modulating configurations.

Examples of alternate configurations include, but are not limited to, the configurations illustrated in FIG. 4. FIG. 4A illustrates a phase modulator 401 with a partially reflective surface 402 and a highly reflective surface 403. A varying voltage 404 (labeled V) modulates the phase modulator thereby imposing multiple depth related frequency components on the composite reference beam. The resulting composite reference beam 405 is combined with the scattered probe signal 406 in the beam splitter 407 to generate the resulting composite interference signal 408 as described earlier.

Another example is illustrated in FIG. 4B where the partially reflective element 409 and the modulating reflective element 410 are both mounted on translation element 411 which can be translated by conventional means in the direction indicated by 412. Translating the translation element at speeds compared to the other modulations enables the depth region that is being scanned or analyzed to be varied.

Yet another example is illustrated in FIG. 4C where a surface 413 of the beam splitter 414 is coated to be partially reflective to form the partially reflective element. The modulating reflective element 415 modulates by being translated be a piezo based device 416, the other end of which is rigidly attached to a mount, such as a structure on the micro-bench. The probe surface of the beam-splitter could include an index matching element or material to facilitate transmitting probe radiation into the target which could be indirect contact with the index matching material.

The index matching material could include deformable material to facilitate moving the target with respect to the beam-splitter. The index matching element could include a replaceable element or portion. The replaceable element (or disposable portion) could facilitate frequent replacement of the surface in contact with the target thereby preventing gradual (or abrupt) degradation of system performance with use. The index matching element, the deformable element and the replaceable element could be separate elements or combined.

The drive signals to modulators could be sine waves, or other generated waveforms that, for example, extend the linear duration of the scan. Other modulators, including but not limited to acousto-optic modulators using transducers could be used. The preferred embodiment could utilize a collimated beam, or a focusing beam. It could use a multi-segment detector for parallel two dimensional spatial detection and could include one or more mask or micro-lens arrays. Alternatively, the micro-bench optical system could be translated parallel to the surface of the target providing two or three dimension imaging and analysis.

The preferred embodiments that are illustrated are free space configurations. Equivalent configurations could also be implemented in optical fiber or in combinations of free space and optical fiber. In such designs or configurations beam splitters could be replaced by fiber couplers. Mirrors could be replaced by fiber reflective elements, such as fiber loops or Bragg gratings.

The preferred embodiment uses an SLD as the optical source, however other broad-band optical sources such as mode-locked lasers could be used. In the case of a mode-locked laser as the source the reference path length and the probe path length have to be either equal or different by an integral number the length corresponding to the repetition period of the repetitive mode-locked pulse train. This is possible because a mode-locked pulse train has a repetitive nature. This enables the opportunity to have a compact micro-bench optical system but a long probe length which facilitates fiber delivery of the probe signal, which in turn facilitates catheter based internal imaging and analysis. Non-optical sources of broadband radiation may be used including, but not limited to, acoustic radiation including ultra-sound radiation, micro-wave radiation, X-radiation, Also, while the preferred embodiment describes imaging and analyzing tissue as the target, the invention provides a general capability of non-invasive imaging and analysis of characteristics of interest in targets under analysis. For example, imaging and analysis for defect monitoring is included or non-invasive analysis of documents or other artifacts to establish authenticity or composition is included.

The preferred embodiment describes a partially reflective element with 50% transmission and 50% reflection. Other designs may be used, for example, 10% transmission and 90% reflection. This reduces the intensity of lower order component reference beams but also reduces the rate at which higher order beams reduce in intensity which enables a larger number of higher order reflections to have significant component reference beams. The partially reflective element could be independently modulated by, for example a second piezo-electric devise.

Many of the features of this invention have functional equivalents that are intended to be included in the invention as taught. For example, the optical source could include multiple SLDs with either over-lapping or non-overlapping wavelength ranges, or, in the case of a mode-locked laser source could be an optically pumped mode-locked laser, or could be a solid state laser, such as a Cr:LiSAF laser optically pumped by a diode laser. The optical source could be passively mode locked by a Kerr lens or by a semiconductor saturable absorber mirror. Gain switched optical sources, with optical feedback to lock modes may also be used.

The optical source could include band-width broadening mechanisms, including, but not limited to, continuum generation. Such continuum generation based techniques include using wave-guide based micro-rings containing highly non-linear material or photonic crystals and non-linear fiber, such as photonic crystal or holy fiber. For purposes of this invention, mode-locked lasers will include gain switched optical sources band-width broadening mechanisms. Other examples will be apparent to persons skilled in the art. The scope of this invention should be determined with reference to the specification, the drawings, the appended claims, along with the full scope of equivalents as applied thereto.

What is claimed is:

1. A method of scanning a target, said method comprising:
generating probe radiation and reference radiation;
imposing different frequency content on different components of said reference radiation to form composite reference radiation;
applying said probe radiation to said target;

capturing at least part of said probe radiation scattered from within said target to form captured scattered probe radiation;

combining said captured scattered probe radiation and said composite reference radiation to form a composite interferometric signal; and processing said composite interferometric signal to achieve a scan of said target wherein said scan includes a composite continuous scan generated from overlapping segmented scans.

2. The method of claim 1, wherein the probe and reference radiation are generated by at least one super-luminescent diode.

3. The method of claim 1, wherein the reference radiation is separated into component reference beams by a partially reflective element.

4. The method of claim 1, wherein component reference radiation is modulated by a length modulator.

5. The method of claim 4, wherein the length modulator is a piezo based device.

6. The method of claim 1, wherein the composite interference signal is processed to provide information related to different regions within the target.

7. The method of claim 1, wherein the signals related to the different component reference radiation are separated by digital signal processing of the detected composite electronic signal.

8. The method of claim 1, wherein said scan of said target includes at least one non-overlapping segmented scan.

9. The method of claim 1, wherein said composite continuous scan is generated from multiple overlapping segmented scans using image reconstruction techniques.

10. The method of claim 1, wherein the scan is processed to provide scattering information.

11. The method of claim 10, wherein the scattering information is analyzed to determine a measurement of an analyte.

12. The method of claim 11, wherein the measurement of an analyte is the concentration level of glucose in tissue.

13. The method of claim 1, wherein the probe radiation is applied to the target through a replaceable element.

14. The method of claim 1, wherein processing the composite interference signal includes amplifying a detected signal with a frequency dependent logarithmic amplifier.

15. The method of claim 1, wherein said probe and said reference radiation are generated by at least one mode-locked laser.

16. The method of claim 1, wherein said component reference radiation is modulated by a phase modulator.

17. The method of claim 1, wherein said different components of said reference radiation are modulated to form said composite reference radiation, such that when said composite reference radiation is combined with said captured scattered probe radiation, interferometric signals with different frequency content are generated.

18. The method of claim 17, further including generating interferometric signals with different frequency content wherein at least some aspects of the different frequency content are harmonically related.

19. The method of claim 17, further including generating interferometric signals with different frequency content wherein the different frequency content is related to different regions within the target.

20. The method of claim 1, wherein the step of processing said composite interferometric signal further includes the step of separating signals related to different components of said reference radiation by means of electronic filtering of said composite interferometric signal.

21. The method of claim 1, wherein the step of processing said composite interferometric signal further includes the step of processing to provide imaging information.

22. The method of claim 1, wherein the step of processing said composite interferometric signal further includes the step of processing to provide registration information, where said registration information pertains to target scan depth.

23. The method of claim 1, wherein the step of processing said composite interferometric signal further includes the step of processing to provide non-imaging analysis information.

24. The method of claim 1, wherein the step of processing said composite interferometric signal further includes the step of processing to provide information relating to tissue characteristics including malignant tissue conditions.

25. The method of claim 1, wherein the step of applying said probe radiation to said target further includes the step of controlling translational elements.

26. The method of claim 1, wherein the step of applying said probe radiation to said target further includes the step of reducing loss of probe radiation, and wherein the step of capturing said probe radiation scattered from within said target further includes the step of reducing loss of scattered probe radiation.

27. An apparatus for scanning a target, said apparatus comprising:

means for generating probe radiation and reference radiation;

means for imposing different frequency content on different components of said reference radiation to form composite reference radiation;

means for applying said probe radiation to said target;

means for capturing at least part of said probe radiation scattered from within said target to form captured scattered probe radiation;

means for combining said captured scattered probe radiation and said composite reference radiation to form a composite interferometric signal; and means for processing said composite interferometric signal to achieve a scan of said target wherein the scan includes a composite continuous scan generated from overlapping segmented scans.

28. The apparatus of claim 27, wherein the means for generating probe radiation and reference radiation is at least one super-luminescent diode.

29. The apparatus of claim 27, wherein the means for generating probe radiation and reference radiation includes a partially reflective element that separates the reference radiation into component reference beams.

30. The apparatus of claim 27, wherein the means for imposing different frequency content on different components of said reference radiation includes a length modulator.

31. The apparatus of claim 30, wherein the length modulator is a piezo based device.

32. The apparatus of claim 27, wherein the means for processing said composite interferometric signal to achieve a scan of said target communicates information related to different regions within the target.

33. The apparatus of claim 27, wherein the means for processing said composite interferometric signal to achieve a scan of said target includes a digital signal processor operable to separate signals related to said different components of said reference radiation.

34. The apparatus of claim 27, wherein the scan includes a non-overlapping segmented scan.

35. The apparatus of claim 27, wherein the composite continuous scan is generated from multiple overlapping segmented scans using image reconstruction techniques.

36. The apparatus of claim 27, wherein the means for processing said composite interferometric signal to achieve a scan of said target communicates scattering information.

37. The apparatus of claim 36, wherein the means for processing said composite interferometric signal to achieve a scan of said target further analyzes scattering information to determine a measurement of an analyte.

38. The apparatus of claim 37, wherein the means for processing said composite interferometric signal to achieve a scan of said target further analyzes scattering information to determine a measurement of an analyte where the analyte is the concentration level of glucose in tissue.

39. The apparatus of claim 27, wherein the means for generating probe radiation and reference radiation further includes a means to control the generating of said reference radiation and applying of said probe radiation so as to select the region of target to be scanned.

40. The apparatus of claim 27, wherein the probe radiation is applied to the target through a replaceable element.

41. The apparatus of claim 27, wherein means for processing the composite interference signal includes means for amplifying a detected signal with a frequency dependent logarithmic amplifier.

42. The apparatus of claim 27, wherein the means for generating probe and reference radiation is at least one mode-locked laser.

43. The apparatus of claim 27, wherein the means for imposing different frequency content on different components of said reference radiation includes a phase modulator.

44. The apparatus of claim 27, wherein the means for imposing different frequency content on said different components of said reference radiation comprises at least one modulator and at least one partial reflective element.

45. The apparatus of claim 44, wherein the means for imposing different frequency content on said different components of said reference radiation comprises at least one modulator and at least one partial reflective element operable to impose harmonically related different frequency content.

46. The apparatus of claim 44, wherein the means for processing said composite interferometric signal to achieve a scan of said target includes an electronic filter operable to separate signals related to said different components of said reference radiation.

47. The apparatus of claim 27, wherein the means for processing said composite interferometric signal scan is operable to provide imaging information.

48. The apparatus of claim 27, wherein the means for processing said composite interferometric signal scan is operable to provide registration information, where said registration information pertains to target scan depth.

49. The apparatus of claim 27, wherein the means for processing said composite interferometric signal scan is operable to provide non-imaging analysis information.

50. The apparatus of claim 27, wherein the means for processing said composite interferometric signal scan is operable to provide information relating to tissue characteristics including malignant tissue conditions.

51. The apparatus of claim 27, wherein means for applying said probe radiation to said target includes an index matching element.

52. The apparatus of claim 27, wherein means for applying said probe radiation to said target includes a deformable element.

* * * * *